United States Patent
Barnich et al.

(10) Patent No.: US 9,176,131 B2
(45) Date of Patent: *Nov. 3, 2015

(54) METHOD FOR DIAGNOSING AND TREATING CROHN'S DISEASE

(75) Inventors: Nicolas Barnich, Ludesse (FR); Arlette Darfeuille-Michaud, La Roche Blanche (FR); Anne-Lise Glasser, Aubiere (FR)

(73) Assignee: LESAFFRE ET COMPAGNIE, Paris (FR)

( * ) Notice: Subject to any disclaimer, the term of this patent is extended or adjusted under 35 U.S.C. 154(b) by 1031 days.

This patent is subject to a terminal disclaimer.

(21) Appl. No.: 11/577,264

(22) PCT Filed: Oct. 13, 2005

(86) PCT No.: PCT/FR2005/002538
§ 371 (c)(1),
(2), (4) Date: Feb. 14, 2008

(87) PCT Pub. No.: WO2006/040481
PCT Pub. Date: Apr. 20, 2006

(65) Prior Publication Data
US 2010/0015600 A1    Jan. 21, 2010

(30) Foreign Application Priority Data
Oct. 14, 2004 (FR) ...................... 04 10865

(51) Int. Cl.
*A01N 37/18* (2006.01)
*G01N 33/567* (2006.01)
*A61K 31/70* (2006.01)
*C07K 16/28* (2006.01)
*G01N 33/68* (2006.01)

(52) U.S. Cl.
CPC .............. *G01N 33/567* (2013.01); *A61K 31/70* (2013.01); *C07K 16/2803* (2013.01); *G01N 33/6893* (2013.01); *C07K 2316/96* (2013.01); *G01N 2333/705* (2013.01); *G01N 2500/00* (2013.01); *G01N 2800/065* (2013.01)

(58) Field of Classification Search
None
See application file for complete search history.

(56) References Cited

U.S. PATENT DOCUMENTS

| | | | |
|---|---|---|---|
| 5,587,364 A * | 12/1996 | McAnalley et al. | 514/54 |
| 6,290,959 B1 | 9/2001 | Wu et al. | |
| 6,942,981 B1 * | 9/2005 | Lu et al. | 435/7.1 |
| 7,799,328 B2 * | 9/2010 | Hublot et al. | 424/195.16 |
| 8,476,058 B2 * | 7/2013 | Simon et al. | 435/255.2 |
| 2004/0005304 A1 | 1/2004 | Brudnak | |
| 2004/0166198 A1* | 8/2004 | Kiers et al. | 426/49 |
| 2005/0075308 A1* | 4/2005 | Wilson et al. | 514/46 |
| 2006/0140973 A1* | 6/2006 | Hublot et al. | 424/195.16 |

FOREIGN PATENT DOCUMENTS

| | | | |
|---|---|---|---|
| WO | WO-97/39356 | 10/1997 | |
| WO | WO/00/33854 * | 6/2000 | |
| WO | WO-03/002117 | 1/2003 | |
| WO | WO 03/002117 A2 * | 1/2003 | ........... A61K 31/455 |
| WO | WO-03/070266 | 8/2003 | |

OTHER PUBLICATIONS

Brest et al., Increased Rate of Apoptosis and Diminished Phagocytic Ability of Human Neutrophils Infected with Afa/Dr Diffusely Adhering Escherichia coli Strains, American Society for Microbiology, Infection and Immunity, Oct. 2004, p. 5741-5749, and published on Oct. 1, 2004 as shown by document V below.*
Brest et al., publication date of Oct. 1, 2004, one page.*
Darfeuille-Michaud, High prevalence of adherent-invasive Escherichia coli associated with ileal mucosa in Crohn's disease, Abstract, Gastroenterology, vol. 127, Issue 2, Aug. 2004, pp. 1-3.*
Guslandi et al. Saccharomyces boulardii in Maintenance Treatment of Crohn's Disease. Digestive Diseases and Sciences, vol. 45, No. 7 (Jul. 2000), pp. 1462-1464.*
The Point Institute Technical Report: Saccharomyces boulardii in Gastrointestinal Related Disorders. Dec. 2008, pp. 1-13.*
Ofek, I., D. Mirelman, and N. Sharon. 1977. Adherence of Escherichia coli to human mucosal cells mediated by mannose receptors. Nature (Lond.). 265: 623-625.*
Darfeulle-Michaud A., Adherent-invasive Escherichia coli: a putative new E. coli pathotype associated with Crohn's disease. Int J Med Microbiol. Sep. 2002;292(3-4):185-93.*
Plein K, Hotz J. Therapeutic effects of Saccharomyces boulardii on mild residual symptoms in a stable phase of Crohn's disease with special respect to chronic diarrhea—a pilot study. Z Gastroenterol. Feb. 1993;31(2):129-34.*
Glasser et al. Adherent invasive Escherichia coli strains from patients with Crohn's disease survive and replicate within macrophages without inducing host cell death. Infect Immun. Sep. 2001;69(9):5529-37.*
Sauter et al, "Identification of the specific oligosaccharide sites recognized by type 1 fimbriae from Escherichia coli on nonspecific cross-reacting antigen, a CD66 cluster granulocyte glycoprotein", 1993, pp. 15510-15516, vol. 268, No. 21, Journal of Biological Chemistry.
Boudeau et al, "Type 1 pili-mediated adherence of Escherichia coli strain LF82 isolated from Crohn's disease is involved in bacterial invasion of intestinal epithelial cells", Mar. 2001, pp. 1272-1284, vol. 39, No. 5, Molecular Microbiology.

(Continued)

*Primary Examiner* — Maher Haddad
(74) *Attorney, Agent, or Firm* — B. Aaron Schulman, Esq.; Stites & Harbison, PLLC.

(57) ABSTRACT

The invention concerns an in vitro method for diagnosing Crohn's disease, or for determining predisposition in a person to develop Crohn's disease, by detecting an overexpression of the CD66c receptor in subjects suffering from said disease or at risk. The invention also concerns preventive or curative treatment of Crohn's disease.

11 Claims, 2 Drawing Sheets

(56) References Cited

OTHER PUBLICATIONS

Database Biosis [Online] Biosciences Information Service, Philadelphia, PA, US; Apr. 2005, Barnich Nicolas et al: "E. coli colonization of the ileal mucosa in patients with Crohn's disease involves type I pili and expression of the glycosylphosphatidylinositol-anchored molecule CEACAM6" XP002386968 Database accession No. PREV200600211501 abstract & Gastroenterology, vol. 128, No. 4, Suppln. 2, Apr. 2005, p. A501, Annual Meeting of the American-Gastroenterological-Association/Digestive-Disease-Week; Chicago, IL, USA; May 14-19, 2005 ISSN: 0016-5085, Only Abstract provided and considered.

* cited by examiner

FIG.2

SEQUENCE LISTING

```
<160> NUMBER OF SEQ ID NOS: 15

<210> SEQ ID NO 1
<211> LENGTH: 20
<212> TYPE: DNA
<213> ORGANISM: Artificial
<220> FEATURE:
<223> OTHER INFORMATION: PCR Primer

<400> SEQUENCE: 1
cctgcagatt gcatgtcccc                                               20

<210> SEQ ID NO 2
<211> LENGTH: 21
<212> TYPE: DNA
<213> ORGANISM: Artificial
<220> FEATURE:
<223> OTHER INFORMATION: PCR primer

<400> SEQUENCE: 2
ccaatacgat tctggggcag g                                             21

<210> SEQ ID NO 3
<211> LENGTH: 13
<212> TYPE: PRT
<213> ORGANISM: Homo sapiens

<400> SEQUENCE: 3

Ser Thr Pro Phe Asn Val Ala Glu Gly Lys Glu Val Leu
1               5                   10

<210> SEQ ID NO 4
<211> LENGTH: 14
<212> TYPE: PRT
<213> ORGANISM: Homo sapiens

<400> SEQUENCE: 4

Leu Ala His Asn Leu Pro Gln Asn Arg Ile Gly Tyr Ser Trp
1               5                   10

<210> SEQ ID NO 5
<211> LENGTH: 14
<212> TYPE: PRT
<213> ORGANISM: Homo sapiens

<400> SEQUENCE: 5

Lys Gly Glu Arg Val Asp Gly Asn Ser Leu Ile Val Gly Tyr
1               5                   10

<210> SEQ ID NO 6
<211> LENGTH: 13
<212> TYPE: PRT
<213> ORGANISM: Homo sapiens

<400> SEQUENCE: 6
```

```
Val Gly Tyr Val Ile Gly Thr Gln Gln Ala Thr Pro Gly
1               5                   10
```

<210> SEQ ID NO 7
<211> LENGTH: 14
<212> TYPE: PRT
<213> ORGANISM: Homo sapiens

<400> SEQUENCE: 7

```
Ala Thr Pro Gly Pro Ala Tyr Ser Gly Arg Glu Thr Ile Tyr
1               5                   10
```

<210> SEQ ID NO 8
<211> LENGTH: 14
<212> TYPE: PRT
<213> ORGANISM: Homo sapiens

<400> SEQUENCE: 8

```
Leu Leu Ile Gln Asn Val Thr Gln Asn Asp Thr Gly Phe Tyr
1               5                   10
```

<210> SEQ ID NO 9
<211> LENGTH: 14
<212> TYPE: PRT
<213> ORGANISM: Homo sapiens

<400> SEQUENCE: 9

```
Val Ile Lys Ser Asp Leu Val Asn Glu Glu Ala Thr Gly Gln
1               5                   10
```

<210> SEQ ID NO 10
<211> LENGTH: 14
<212> TYPE: PRT
<213> ORGANISM: Homo sapiens

<400> SEQUENCE: 10

```
Glu Ala Thr Gly Gln Phe His Val Tyr Pro Glu Leu Pro Lys
1               5                   10
```

<210> SEQ ID NO 11
<211> LENGTH: 14
<212> TYPE: PRT
<213> ORGANISM: Homo sapiens

<400> SEQUENCE: 11

```
Asn Asn Ser Asn Pro Val Glu Asp Lys Asp Ala Val Ala Phe
1               5                   10
```

<210> SEQ ID NO 12
<211> LENGTH: 14
<212> TYPE: PRT
<213> ORGANISM: Homo sapiens

<400> SEQUENCE: 12

```
Pro Glu Val Gln Asn Thr Thr Tyr Leu Trp Trp Val Asn Gly
1               5                   10
```

<210> SEQ ID NO 13
<211> LENGTH: 14
<212> TYPE: PRT
<213> ORGANISM: Homo sapiens

<400> SEQUENCE: 13

```
Asn Gly Gln Ser Leu Pro Val Ser Pro Arg Leu Gln Leu Ser
1               5                   10
```

```
<210> SEQ ID NO 14
<211> LENGTH: 14
<212> TYPE: PRT
<213> ORGANISM: Homo sapiens

<400> SEQUENCE: 14

Leu Gln Leu Ser Asn Gly Asn Met Thr Leu Thr Leu Leu Ser
1               5                   10

<210> SEQ ID NO 15
<211> LENGTH: 14
<212> TYPE: PRT
<213> ORGANISM: Homo sapiens

<400> SEQUENCE: 15

Thr Leu Leu Ser Val Lys Arg Asn Asp Ala Gly Ser Tyr Glu
1               5                   10
```

METHOD FOR DIAGNOSING AND TREATING CROHN'S DISEASE

The invention relates to the field of the in vitro diagnosis of Crohn's disease. It makes it possible both to diagnose the presence of the disease and to determine the predisposition of a person to develop the disease. It also relates to the preventive or curative treatment of this disease.

Crohn's disease, which was described in 1932 by Crohn et al., is characterized by a hyperactivation state of the immune system of the intestine, progressing through flare-ups interrupted by periods of remission of varying durations. The incidence in France, expressed as number of new cases per year per $10^5$ inhabitants, is estimated at $100/10^5$ inhabitants. In 2004, more than 100 000 cases were recorded in France.

Crohn's disease (CD) manifests itself clinically by abdominal pain, diarrhea, fever and undernourishment. Signs of extra-digestive (articular, skin or ocular) inflammation are frequently associated. Diagnosis is based on the clinical state, endoscopy, ileo-colic biopsies and radiology of the small intestine. The clinical, endoscopic and anatomo-pathological picture has no specificity, and the establishment of the diagnosis requires excluding all the other curable conditions giving a similar picture (Colombel and Menard, 1993). Biological tests are used for the diagnosis and monitoring of Crohn's disease, including the following markers: ANCA (perinuclear anti-neutrophilic antibody), ASCA (anti-*Saccharomyces cerevisiae* antibody) and anti-OmpC (outer membrane porin C from *E. coli*). These markers are not specific for Crohn's disease and a negative test cannot rule out the possibility of Crohn's disease (Nakamura et al., 2003).

Crohn's disease constitutes one of the major hepato-gastro-enterology problems because it does not have a specific treatment. It is a highly incapacitating disease which is controlled to a greater or lesser degree by corticoids, immunosuppressants, nutritional assistance and surgery. The treatment is mainly based on symptomatic data and is only suspensive because it never results in a complete cure for the patient. The main functions of this treatment are to control the flare-ups and then to prevent recurrence. Briefly, the medicaments used can be divided into two categories: anti-inflammatories such as salicylated derivatives or corticoids, and immunosuppressants. However, these treatments often prove ineffective and surgical resections are unavoidable in 90% of cases. Recently, infliximab, a monoclonal anti-TNFα antibody, was found to be effective for the treatment of some patients presenting a severe clinical picture and not responding to conventional treatments (Rutgeerts et al., 1999, Present et al., 1999). However, this treatment has limits. Indeed, patients treated with infliximab sometimes produce anti-infliximab antibodies, thus reducing the duration of response to the treatment (Baert et al., 2003). Furthermore, some patients subjected to this treatment developed a serious infectious pathology of the tuberculosis, aspergillosis and candidiasis type (Wallis et al., 2004).

The etiology of Crohn's disease has not yet been clearly elucidated. Several factors influencing the survival, the maintenance or the worsening of Crohn's disease have been envisaged. They are in particular environmental, immune, genetic and infectious factors (Podolsky 2002, Shanahan 2002).

Crohn's disease is characterized by a state of hyperactivation of the immune system at the intestinal level which results in recruitment and activation of the lymphocytes and the macrophages. It is now well established that pro-inflammatory cytokines such as interleukin-1 (Il-1), Il-6, Il-8 and TNF-α released in large quantities in the intestinal mucosa of patients suffering from Crohn's disease are responsible for inducing intestinal inflammation (Desreumaux et al., 1997).

Many clinical, experimental and epidemiological arguments suggest the involvement of infectious agents in the genesis and/or maintenance of Crohn's disease lesions (Sartor et al., 1996). The regular progression of the disease, its distribution into sometimes very active foci, and the appearance of familial cases of Crohn's disease involving unrelated married couples and their children suggest the role of a transmissible infectious agent (Bennett et al., 1991).

The study of *E. coli* strains isolated from ileal biopsies of patients suffering from Crohn's disease has shown that the acute and chronic ileal lesions in Crohn's disease were abnormally colonized by *E. coli* strains (representing up to 100% of the total flora). These strains lack the virulence genes conventionally found in various *E. coli* pathovars responsible for intestinal infections. The majority (80%) of these strains possess a high power for adhesion in vitro to the intestinal epithelial cells Caco-2 and a relationship has been established between adhesion power and level of colonization of the intestinal mucosa (Darfeuille-Michaud et al., 1998).

The *E. coli* strain LF82, isolated from a chronic ileal lesion in a patient suffering from Crohn's disease, possesses all the characteristics of an invasive bacterial pathogen: (i) the bacteria are internalized by epithelial cells in culture with a level of internalization similar to those of *Shigella*, (ii) its active entry process depends both on the microtubules and a polymerization of actin, and (iii) it is capable of surviving and of multiplying in the cytoplasm of the host cell after lysis of the endocytosis vacuole.

The characterization of an adhesion-invasion phenotype of the LF82 strain and the absence of genetic determinants of invasion already described in *E. coli*, *Shigella* and *Salmonella* has led to the existence of a novel group of *E. coli* pathogen being defined which can be associated with Crohn's disease, designated AIEC for "adherent-invasive *E. coli*" (Boudeau et al., 1999). These AIEC strains are thought to colonize the intestinal mucosa of patients by adhering to the brush border of the enterocytes (Darfeuille-Michaud, 2002). Their prevalence is 36.4% at the level of the acute ileal lesions of patients suffering from Crohn's disease (Darfeuille-Michaud et al., 2004).

One of the histological characteristics of Crohn's disease is the presence of granulomas in 50 to 87% of cases. A granulomatous inflammation is found in some bacterial infections such as salmonellosis, yersiniosis or paratuberculosis, calling into play invasive bacteria also having the capacity to resist the bactericidal power of the macrophages. Recently, the presence of *Escherichia coli* DNA in the granulomas has been shown in 80% of patients suffering from CD, confirming the infectious route involving *E. coli* (Ryan et al., 2004). After phagocytosis by murine or human macrophages in vitro, the AIEC strain LF82 survives and multiplies in a large vacuole, while preserving the integrity of the host cell. Following infection, the macrophages secrete a large quantity of TNFα. Thus, the AIEC strains are capable not only of invading the epithelial cells but also possess genetic determinants allowing them to resist the bactericidal action of the macrophages (Glasser et al., 2001).

Ribotyping studies were not able to demonstrate the presence of a single strain; on the other hand AIEC strains isolated from chronic lesions or recidivations exhibit an identical ribotyping profile or belong to a common group. These genetically linked strains are thought to have evolved from the same ancestor by acquisition of virulence factors by horizontal transfer of genes or insertion of pathogenicity islands in the bacterial chromosome (Masseret et al., 2001).

It has in addition been shown, in an in vitro model of intestinal epithelial cells, that the type 1 pili are involved in the adhesion of AIEC bacteria to the cells and also in the active internalization of bacteria by inducing the formation of membrane elongations by the infected cell (Boudeau et al., 2001).

The process for adhesion of a bacterium to eukaryotic cells results from a specific interaction between a ligand of the bacterial surface called adhesin and a cell receptor (Beachey et al., 1981). The receptors involved in the adhesion of E. coli strains via the type 1 pili described up until now are glycosylphosphatidylinositol (GPI) anchored glycoproteins (Guignot et al., 2000; Leusch et al., 1990; Malaviya et al., 1999; Nowicki et al., 1993). The adhesin FimH of type 1 pili recognizes the GPI-anchored receptors CD48 and CEACAM6 (CD66c) (Shin et al., 1999; Shin et al., 2000; Sauter et al., 1991; Sauter et al., 1993). The CD66c glycoprotein (CEACAM6, or also called NCA for "Non-specific Cross-reacting Antigen") belongs to the immunoglobulin family, characterized by variable domains in the N-terminal part of the protein, and constant domains containing disulfide bridges inducing the formation of loops (Hammarström and Baranov 2001). CD66c is normally expressed at the surface of the granulocytes, macrophages and polynuclear neutrophils, but also by the epithelial cells in the colon, the lungs and the spleen (Audette et al., 1987; Kolbinger et al., 1989; von Kleist et al., 1972; Jantscheff et al., 2003).

Because of the seriousness of the condition and the current difficulties concerning its diagnosis, an early and reliable diagnosis of predisposition to Crohn's disease or of a Crohn's disease case is obviously very highly desirable. It would contribute toward avoiding the very long waiting times, which always penalize the patients, currently between the management of the patient and the establishment of the diagnosis after excluding all the other conditions giving a similar clinical picture.

Finally, there is also a need for a method which makes it possible to prevent Crohn's disease and/or to treat this disease, which is better targeted than the methods currently used.

The authors of the present invention therefore focussed on developing alternative methods for the diagnosis and therapeutic treatment of Crohn's disease. At the heart of the invention is the demonstration, made by the inventors, of an abnormal overexpression of the CD66c receptor at the ileal level in patients suffering from Crohn's disease and of a remarkable affinity between this receptor and the E. coli AIEC strains. The data obtained by the inventors show, on the one hand, that the receptor is overexpressed at the level of the brush border of the enterocytes and, on the other hand, that the type AIEC E. coli strains have a very high affinity for these receptors, which would explain the colonization of the ileal mucosa by the AIEC bacteria. The adhesion of the AIEC strains to the CD66c receptor occurs via the type 1 pili. The reference strain for this AIEC group, namely the LF82 strain, expresses type 1 pili variants having several amino acid substitutions in the major subunit FirA, in the minor subunits FimI and FimF and in the adhesin FimH (J. Boudeau et al., 2001). The authors of the present invention observed in addition that 51% of the E. coli strains isolated from patients suffering from Crohn's disease had type 1 pili variants, having amino acid substitutions in FimH similar to those observed for FimH of the reference LF82 strain. These type 1 pili variants are therefore thought to be responsible for the higher affinity of these strains for the CD66c receptor.

Diagnostic Applications

The subject of the present invention is therefore an in vitro method for the diagnosis of Crohn's disease, or for the determination of a predisposition of a person to develop Crohn's disease, in which it is determined whether the level of expression of the CD66c receptor in a biological sample from a subject to be tested is higher than the level of expression of a control sample, which is indicative of Crohn's disease, or of a predisposition of the subject tested to develop Crohn's disease.

In the context of the invention, a "biological sample" may be an ileal biopsy or a preparation of enterocytes isolated from an ileal biopsy. The expression "ileal biopsy" is understood to mean a sample of part of the ileum or of the ileal mucosa, for example obtained during surgical resection (the expression surgical item, removed from the ileum, is used in this case) or during endoscopy. The biological sample may also be a sample of a biological fluid, such as blood or serum, or alternatively a stool sample.

When the method of the invention is carried out on a biological sample other than an ileal biopsy or a preparation of isolated enterocytes—namely in particular when the biological sample is a blood or stool sample—, it is advantageous to combine the detection of CD66c with a (quantitative or semiquantitative) detection of tumor markers such as CEA ("carcinonoembryonic antigen") (Grunert et al., 1995). Thus, it is possible to directly distinguish between patients suffering from colorectal cancers and patients suffering from Crohn's disease.

The method of the invention involves either the quantitative determination of the absolute level of expression of the CD66c receptor, and then comparing with the level of expression of the receptor in a control subject, determined in parallel or otherwise known, or the direct determination of the relative level of expression of the CD66c receptor in the biological sample to be tested compared with the control sample (the expression semiquantitative detection may be used in this case). The "control" sample is a sample from a "healthy" subject or a subject not suffering from Crohn's disease, or a subject not suffering from any inflammatory bowel disease (IBD) or from colorectal cancer. This may, depending on the case, be a subject having inflammatory lesions of the small intestine of traumatic or infectious origin. In order to determine the progression of Crohn's disease, it may be useful to determine in a subject the level of expression of CD66c, and to control the effect of a medicament or the development of the disease, by testing the subject a second time, for example several weeks later. In this case, the results of the second test are compared with the results of the first test and in general also with the results obtained in a "healthy" subject. The "control" sample thus refers either to the same test subject or to the "healthy" subject.

A "subject" or "patient" is a mammal, preferably a human being, regardless of sex, age and general condition. Children are also included. The test subject may be asymptomatic, or may be considered as being at risk of developing Crohn's disease.

The term "diagnosis" refers to the determination or the confirmation of infection with Crohn's disease, regardless of its stage of development. This may be more particularly an early diagnosis or a diagnosis of recidivation.

The level of expression of the CD66c receptor may be determined in various ways. It may be determined in particular by assaying the CD66c receptor or by determining its level of transcription, that is to say the quantity of mRNA which codes for the receptor. It may also be determined by the detection and/or quantification of mannose units, in which CD66c is rich. Various methods for the detection and/or quantification of the expression of the CD66c receptor are described below.

According to a first embodiment, the level of expression of the CD66c receptor is determined by measuring the quantity of CD66c receptor protein, generally by bringing a biological sample into contact with a binding partner capable of selectively interacting with the CD66c receptor present in the sample. The binding partner is generally an antibody, which may be polyclonal or monoclonal, preferably monoclonal. This may also be a peptide fragment of the CD66c receptor, such as one of the peptides described in patent application WO 01/013937, and reported in Table 1 below:

TABLE 1

(SEQ ID NOS: 3-15)

| Name of the peptide | Peptide sequence |
|---|---|
| CD66c-1 | STPFNVAEGKEVL |
| CD66c-2 | LAHNLPQNRIGYSW |
| CD66c-3 | KGERVDGNSLIVGY |
| CD66c-4 | VGYVIGTQQATPG |
| CD66c-5 | ATPGPAYSGRETIY |
| CD66c-6 | LLIQNVTQNDTGFY |
| CD66c-7 | VIKSDLVNEEATGQ |
| CD66c-8 | EATGQFHVYPELPK |
| CD66c-9 | NNSNPVEDKDAVAF |
| CD66c-10 | PEVQNTTYLWWVNG |
| CD66c-11 | NGQSLPVSPRLQLS |
| CD66c-12 | LQLSNGNMTLTLLS |
| CD66c-13 | TLLSVKRNDAGSYE |

Antibodies

The term "antibody" refers to any full-length antibody or functional fragment of an antibody (obtained by genetic engineering or not), comprising, or consisting of, at least one antigenic combination site, allowing said antibody to bind to at least one antigenic determinant of an antigenic compound. By way of example of antibody fragments, there may be mentioned the fragments Fab, Fab', F(ab')$_2$ and the single-chain variable fragments (scFv chains).

The expression "capture antibody" is understood to mean an antibody or an antibody part, preferably attached to a solid phase, which is capable of retaining the CD66c antigen present in a biological sample, by affinity binding.

The presence of the antigen in the biological sample is revealed by "detection means". As regards the detection of the antigen, the invention provides in particular for detection with the aid of at least one "detection antibody". Such a labeled, detection antibody is capable of binding to the captured antigen, by affinity binding, by recognizing an epitope site different from that recognized by the capture antibody.

The term "labeled" refers both to a direct labeling (via enzymes, radioisotopes, fluorochromes, luminescent compounds and the like) and to indirect labeling (for example via antibodies which are themselves directly labeled or with the aid of reagents of a labeled "affinity pair" such as, but not exclusively, the labeled avidin-biotin pair, and the like).

The expression "antigenic fragment" is understood to mean any part of CD66c capable of inducing the synthesis of an antibody which is substantially specific for CD66c alone in an immunized animal.

The term "specifically", when it refers to recognition or specific binding of an antibody for an antigen, means that the antibody interacts with the antigen without substantial interaction with other antigens.

The anti-CD66c antibodies used in the present invention are antibodies specific for the antigen. They are preferably monoclonal antibodies or monospecific polyclonal antibodies, that is to say that they specifically recognize only one epitope.

The production of monoclonal antibodies or of monospecific polyclonal sera, or of antibodies obtained by screening genomic libraries, useful in the context of the invention are conventional techniques.

An anti-CD66c polyclonal antibody may, inter alia, be obtained by immunizing an animal such as a rabbit, a mouse and the like with the aid of the soluble CD66c receptor or of an antigenic fragment thereof, collecting and then depleting the antiserum obtained on, for example, an immunoadsorbent containing the receptor according to methods known per se to a person skilled in the art.

Several monoclonal antibodies have been developed and marketed. It is thus possible to use the anti-CD66c monoclonal antibody clone 9A6 (Genovac, Switzerland) or the anti-CD66c monoclonal antibody from InnoGenex, Menarini Diagnostics, (Anthony, France).

Generally, other monoclonal antibodies may be obtained according to the conventional method of lymphocyte fusion and hybridoma culture described by Köhler and Milstein, (1975). Other methods for preparing monoclonal antibodies are also known (Harlow et al., ed., 1988 "Antibodies: a laboratory manual"). The monoclonal antibodies may be prepared by immunizing a mammal (for example a mouse, a rat, a rabbit or even a human being, and the like) and using the lymphocyte fusion technique leading to hybridomas (Köhler and Milstein, 1975).

Alternative techniques to this customary technique exist. It is possible, for example, to produce monoclonal antibodies by expressing a nucleic acid cloned from a hybridoma. It is also possible to produce antibodies by the phage display technique by introducing cDNAs for antibodies into vectors, which are typically filamentous phages which exhibit gene libraries V at the surface of the phage (for example fUSE5 for E. coli, Scott, 1990). Protocols for constructing these antibody libraries are described in Marks et al., (1991).

Kits and reagents useful for the detection of CD66c in a biological sample, in accordance with the method of the invention, may be provided for an easy practical implementation of the invention applicable to numerous biological samples.

Kits for the detection of CD66c in a biological sample may contain at least one antibody as defined above.

Immunological Tests

The quantity of CD66c receptor glycoprotein is thus preferably measured by an immunological test comprising bringing the biological sample into contact with an optionally labeled anti-CD66c antibody which specifically recognizes CD66c, and revealing the antibody-CD66c receptor complexes formed.

For example, the presence of CD66c may be detected using standard electrophoretic and immunodiagnostic techniques, including immunoassays, for example by competition, direct reaction or of the sandwich type. Such assays include in particular Western blots, agglutination tests, enzyme-linked immunosorbent assays (ELISA), avidin/biotin-type assays, radioimmunoassays, immunoelectrophoreses, immunoprecipitations, and the like. The reactions generally include visualization of markers such as fluorescent, chemiluminescent or radioactive molecules or enzymatic markers, or alternatively dyes.

The diagnostic method according to the invention may be carried out according to various formats well known to a person skilled in the art: in solid phase or in homogeneous phase; in a single step or in two steps; as a sandwich method or as a competitive method, as nonlimiting examples.

According to a preferred embodiment, the capture antibody is immobilized on a solid phase. It is possible to use, as nonlimiting examples of solid phase, microplates, in particular polystyrene microplates, such as those marketed by the company Nunc, Denmark. It is also possible to use solid particles or beads, paramagnetic beads, such as those provided by Dynal or Merck-Eurolab (France) (under the brand Estapor™) or alternatively polystyrene or polypropylene test tubes, and the like.

A sandwich-type immunoassay format between two (capture and detection) antibodies is particularly advantageous for the detection of the antigens present in the biological sample, when the latter is a biological fluid such as blood, or a stool sample for example.

An immunoassay format for detection of antigens by competition is also possible. Other immunoassay modes can also be envisaged and are well known to a person skilled in the art.

ELISA assays, radioimmunoassays, or any other detection technique may be used to reveal the presence of the antigen-antibody complexes formed.

According to a preferred embodiment, an in vitro method for the diagnosis of Crohn's disease comprises an immunological test, for example of the ELISA test type, on a blood or stool sample. It is thus possible to use an immunological plate assay, with an attached capture antibody CD66abce, and various dilutions of blood or stool, the CD66c antigen being revealed by a specific revealing antibody, namely a labeled anti-CD66c antibody, for example coupled to an enzyme or a fluorochrome. The anti-CD66c antibody may be for example the mouse anti-human CD66abce monoclonal antibody from DAKO (clone Kat4C, DAKO, Denmark). It is also possible to use concanavalin A in place of the attached antibody, to capture the anti-CD66c receptor by its mannose units.

Alternatively, the level of expression of the CD66c receptor is determined by measuring the level of production of anti-CD66c antibodies. The level of expression of anti-CD66c antibodies may be determined, preferably in a blood or stool sample, by bringing the sample into contact with an optionally attached CD66c antigen, or an epitope fragment thereof, and revealing the antibody-CD66c receptor complexes formed. It is thus possible to use an immunological plate assay with the attached CD66c antigen and various dilutions of blood or stool, the anti-CD66c antibodies being revealed with a labeled anti-IgG, or anti-IgA, or alternatively anti-IgM antibody, for example coupled to an enzyme or a fluorochrome.

According to another embodiment, the method of the invention comprises an immunohistochemical test carried out on an ileal biopsy.

For example, fixed ileal biopsy sections may be labeled with an anti-CD66c antibody, and then revealed with a secondary antibody coupled to a fluorochrome or to a peroxidase or alkaline phosphatase type enzyme. The expression of the CD66c receptor may be interpreted, after microscope observation or electronic reading, and classified according to an anatomopathological score between 0 (absence of expression) and 4 (very high expression at the cytoplasmic and brush border level), indicating the stage of progression of the disease.

Alternatively, labeling tests may be carried out by bringing preparations of enterocytes isolated from an ileal biopsy into contact with an anti-CD66c antibody directly detectably labeled, for example, with an FITC or Alexa Fluor 488 or 647 type fluorochrome. The specific labeling of the CD66c receptors overexpressed at the level of the brush border of the enterocytes in the case of Crohn's disease is thus visualized.

Detection of the Mannose Units

According to another embodiment of the invention, the level of expression of the CD66c receptor is determined indirectly by the quantitative detection of the mannose units present at the level of the brush border of the enterocytes. This type of test is particularly practical to carry out on ileal biopsies or preparations of isolated enterocytes.

It makes it possible to easily demonstrate the overexpression of the CD66c receptors, which are highly mannosylated, at the level of the brush border of the enterocytes. For example, the quantitative or semiquantitative detection of the mannose units may be carried out by bringing the biological sample into contact with a lectin such as concanavalin A labeled detectably, and revealing the complexes formed by the concanavalin A bound to the mannose units. The concanavalin A may for example be coupled to a fluorochrome, such as FITC.

RNA Tests

According to another embodiment of the invention, the level of expression of the CD66c receptor is determined by measuring the quantity of mRNA for CD66c in the biological sample.

Methods for determining the level of transcription of a gene are well known. For example, the nucleic acid contained in the samples (for example a preparation of enterocytes or an ileal biopsy), is generally first extracted according to standard methods, for example with the aid of lytic enzymes, or chemical solutions by resins binding the nucleic acids. The mRNA extracted is then detected by hybridization (for example by Northern-blot analysis) and/or amplification after reverse transcription (RT-PCR), with the aid of specific oligonucleotide primers. An example of specific primers which can be used is given below:

```
                                         (SEQ ID No. 1)
CD66c F:  5' CCTGCAGATTGCATGTCCCC (SEQ ID No. 2)
CD66c R:  5' CCAATACGATTCTGGGGCAGG
```

In a particular exemplary embodiment, the biological sample is an ileal biopsy or a preparation of isolated enterocytes and the quantity of mRNA for CD66c is measured by real-time RT-PCR, preferably after extraction of the total RNA.

Therapeutical Applications

Another aspect of the invention provides therapeutic methods for the prevention or treatment of Crohn's disease. These methods are based on the demonstration that the CD66c receptor is overexpressed in patients suffering from Crohn's disease and is responsible for the binding of the *Escherichia coli* AIEC bacteria to the brush border of the enterocytes. Any agent specifically inhibiting the interaction between the CD66c receptor and the *E. coli* AIEC strains is therefore useful for the prevention or treatment of Crohn's disease.

The invention therefore also relates to the use of an agent specifically inhibiting the interaction between the CD66c receptor and the *Escherichia coli* AIEC strains, for the manufacture of a medicament intended for the prevention or treatment of Crohn's disease.

This agent may be an anti-CD66c inhibitor antibody which specifically recognizes the CD66c receptor and blocks the binding of this receptor with an *E. coli* AIEC strain.

Said agent may be alternatively a CD66c receptor glycoprotein or a synthetic glycoprotein mimicking CD66c.

It may also be a peptide fragment of the CD66c receptor, such as one of the peptides described in patent application WO 01/013937, and presented above.

The agent may also be a mannoside, such as D-mannose, methyl-D-mannose, or a particle carrying one or more mannose units. By definition, the term mannoside therefore includes D-mannose and the compounds capable of releasing D-mannose by hydrolysis, for example polysaccharides and oligosaccharides which release D-mannose by hydrolysis (homo- or heterosaccharides), and any derivatives of D-mannose capable of interacting with the adhesin FimH of the AIEC strains. The particles carrying one or more mannose units may be for example inert beads or particles or living or dead cells.

More particularly, the agent used may be an agent which specifically blocks the interaction between the CD66c receptor and the adhesin FimH of the AIEC strains.

The invention moreover provides an in vitro method for screening candidate substances for the prevention or treatment of Crohn's disease, comprising:
(i) bringing the CD66c receptor expressed at the surface of a cell into contact with at least one *Escherichia coli* AIEC strain, in the presence or in the absence of a substance to be tested;
(ii) determining the capacity of the substance to specifically inhibit the interaction between the CD66c receptor and said strain, and selecting and/or identifying said substance.

Candidate substances may be of any type, including natural or synthetic compounds or mixtures of compounds. The substance may be structurally defined or of an unknown structure, for example in the form of a biological extract.

To determine the capacity of the candidate substance to inhibit the binding between the *E. coli* AIEC strains and the CD66c receptor, standard competition tests may be performed on cell cultures expressing the CD66c receptor. This may be, for example, cells genetically transformed in order to overexpress the receptor, or enterocytes isolated from the ileal biopsy of patients suffering from Crohn's disease. They may be intestinal epithelial cells cultured in monolayers (by way of example HT29, Caco-2, T84, intestine-407 cells). In the case where the candidate substance is an identified compound, it may be labeled, for example with a radioactive or nonradioactive marker (for example fluorescein).

The marker specifically bound to the CD66c receptor may then be quantified in the presence of a variable concentration of said candidate substance, for example from $10^{-10}$ to $10^{-5}$ M. Alternatively, it is possible to monitor the competition between the candidate substance and the *E. coli* AIEC bacterium toward the CD66c receptor by adhesion tests.

The agents which specifically inhibit the interaction between the CD66c receptor and the *E. coli* AIEC strains may be formulated in the form of a pharmaceutical composition, preferably for oral administration.

These compositions may be administered orally for example, for example in the form of tablets, capsules or granules with immediate or controlled release.

A solid composition for oral administration is prepared by adding to the active ingredient a filler and, where appropriate, a binder, a disintegrating agent, a lubricant, a colorant or a flavor corrigent, and by forming the mixture into a tablet, a coated tablet, a granule, a powder or a capsule.

Examples of fillers include lactose, corn starch, sucrose, glucose, sorbitol, crystalline cellulose and silicon dioxide, and examples of binders include poly(vinyl alcohol), poly (vinyl ether), ethylcellulose, methylcellulose, acacia, gum tragacanth, gelatin, shellac, hydroxypropylcellulose, hydroxypropylmethyl-cellulose, calcium citrate, dextrin and pectin.

Examples of lubricants include magnesium stearate, talc, polyethylene glycol, silica and hardened vegetable oils. The colorant may be any one of those authorized for use in medicaments.

Examples of flavor corrigents comprise powdered cocoa, mint in herb form, aromatic powder, mint in oil form, borneol and powdered cinnamon. It should be understood that the tablet or granule may be suitably coated with sugar, gelatin or the like.

The effective doses and dosages for administration of the therapeutic agents, intended for the prevention or treatment of Crohn's disease, depend on a large number of factors, and for example on the nature of the agent, the size of the patient, the stage of the disease, the specific pharmaceutical composition used and the observations and conclusions of the attending physician.

For example, in the case of an oral administration, for example a tablet or a capsule, a possible suitable dosage is between about 0.1 mg/kg and about 100 mg/kg of body weight per day, and preferably between about 0.5 mg/kg and about 50 mg/kg of body weight per day, more preferably between about 1 mg/kg and about 10 mg/kg of body weight per day and preferably still between about 2 mg/kg and about 5 mg/kg of body weight per day of active material.

If representative body weights of 10 kg and 100 kg are considered in order to illustrate the daily dosage range by the oral route which may be used as described above, suitable dosages will be between about 1-10 mg and 1000-10 000 mg per day, preferably between about 5-50 mg and 500-5000 mg per day, preferably still between about 10.0-100.0 mg and 100.0-1000.0 mg per day, and more preferably between about 20.0-200.0 mg and about 50.0-500.0 mg per day, of active ingredient.

These dosage ranges represent total quantities of active ingredient per day for a given patient. The number of administrations per day at which a dose is administered may vary widely, especially according to pharmacokinetic factors.

The following figures and examples illustrate the invention without limiting its scope.

LEGEND TO THE FIGURES

FIGS. 1A and 1C are sections for mucosa with no inflammation, and FIGS. 1B and 1D are sections for mucosa with inflammation as demonstrated by the presence of infiltrated polynuclear neutrophils. FIG. 1A shows no labeling with the anti-CD66c antibody, indicating that this glycoprotein is not expressed in healthy tissue. It should be noted that even in tissue exhibiting signs of inflammation (FIG. 1B) from a subject not suffering from Crohn's disease whose intestinal inflammation is of traumatic origin (post-operative adhesive small bowel perforation), no labeling with the CD66c antibody is observed. Thus, the presence of the CD66c glycoprotein at the ileal level is not linked to the inflammatory status of the mucosa. FIG. 1C demonstrates expression of CD66c at the level of the brush border of the enterocytes of a patient suffering from Crohn's disease. This expression is observed in the absence of inflammation at the level of a nonulcerated mucosa. FIG. 1D presents a hyperexpression of CD66c at the level of the brush border of the enterocytes and a cytoplasmic expression of this protein in an inflammatory and lesioned region in a patient suffering from Crohn's disease. Immunolabeling is performed with the aid of anti-CD66c antibodies labeled with the avidin-biotin peroxidase complex, coupled to a chromogen.

EXAMPLES

Example 1

Identification of CD66c as a Specific Receptor for the AIEC Bacteria Involved in Crohn's Disease A. Bacterial Strains and Culture The *E. coli* LF82 strain, isolated from a chronic ileal lesion from a patient suffering from Crohn's disease, is used as reference strain (Adherent-Invasive *E. coli*). This strain is described in J. Boudeau et al. (1999). It adheres and invades intestinal epithelial cells in culture and replicates in the cytoplasm of the host cells after lysis of the endocytosis vacuoles. It is capable of surviving and replicating in the murine macrophages J774-A1 by inducing a high secretion of proinflammatory cytokine TNF-alpha. It also multiplies in mouse peritoneal macrophages and in human macrophages derived from monocytes.

Mutants of the LF82 strain were also used which do not express type 1 pili following insertion of the transposon Tn5phoA into the fimA gene (mutant 52D11) or into the fimH gene (mutant ZG2) of the fim operon encoding the type 1 pili, as described in J. Boudeau et al. (2001).

The bacteria are cultured in Luria-Bertani (LB) broth or on LB or Mueller-Hinton (MH) agar plates (Institut Pasteur Production, Marnes-la-Coquette, France).

B. Ileal Samples from Patients Suffering from CD and from Healthy Controls

Enterocytes were isolated from ileal surgical parts obtained by surgery or by ileal endoscopic biopsies from 12 patients suffering from Crohn's disease (CD patients) and 7 subjects without inflammatory bowel disease (IBD). The samples were frozen at −80° C. in modified Eagle's medium (MEM, Seromed, Biochrom, Berlin, Germany) containing 10% glycerol and 10% dimethyl sulfoxide (DMSO, Sigma Chemical Company, St-Louis, Mo.) immediately after collection.

C. Adhesion In Vitro to the Isolated Enterocytes

The adhesion trials were performed as described in Darfeuille-Michaud et al., (1990); S. Knutton et al., (1985) and B. Lafeuille et al., (1981). The frozen intestinal samples were washed 3 times in PBS and the ileal mucosa was scraped with a cover glass in order to detach the enterocytes in PBS buffer supplemented with 0.25 M EDTA. About $10^5$ isolated enterocytes were mixed with $10^8$ *E. coli* cells in MEM medium containing 10% fetal calf serum (FCS, Seromed). After incubating for 2 hours at 37° C. and with gentle stirring, the enterocytes were washed 3 times in PBS (pH 7.2). The adhesion of the bacteria was quantified by examining under a phase contrast microscope at magnification×1000. The counting was performed according to a double blind design in order to determine the number of *E. coli* adhering to the brush border of 30 to 50 enterocytes. The adhesion index is expressed as number of bacteria attached to the brush border of one enterocyte.

In the case of the enterocytes obtained from patients, the observed adhesion index ranged from 0.542 to 1.999 against 0.096 to 0.511 for the controls (Table 2).

TABLE 2

Index of adhesion of the bacteria to the enterocytes

| | Adhesion index[a] | |
|---|---|---|
| | Mean | Standard deviation |
| CD patients | | |
| Patient 1 | 1.999 | 0.459 |
| Patient 2 | 1.429 | 0.106 |
| Patient 3 | 1.352 | 0.101 |
| Patient 4 | 1.599 | 0.294 |
| Patient 5 | 1.459 | 0.196 |
| Patient 6 | 1.426 | 0.417 |
| Patient 7 | 0.768 | 0.167 |
| Patient 8 | 0.542 | 0.090 |
| Patient 9 | 0.551 | 0.083 |
| Patient 10 | 1.404 | 0.092 |
| Patient 11 | 1.056 | 0.347 |
| Patient 12 | 0.708 | 0.337 |
| Patient 13 | 1.017 | 0.117 |
| Healthy subjects | | |
| Subject 1 | 0.208 | 0.084 |
| Subject 2 | 0.096 | 0.021 |
| Subject 3 | 0.133 | 0.030 |
| Subject 4 | 0.380 | 0.020 |
| Subject 5 | 0.240 | 0.030 |
| Subject 6 | 0.222 | 0.028 |
| Subject 7 | 0.511 | 0.035 |

[a]mean number of bacteria adhering to the brush border of an enterocyte.

An adhesion index greater than 1 is considered as indicative of an effective adhesion to the brush border (S. Knutton et al., (1985); B. Larfeuille et al., (1981)). In the experiment, indices of greater than 1 were observed with the enterocytes from 9 CD patients out of 13, that is 69%, and no index greater than 1 was observed for the controls. The capacity of the LF82 strain to adhere to the brush border of the enterocytes is significantly higher with the enterocytes isolated from CD patients than with the controls (P=0.006). This led to the consideration that the CD patients could express a receptor located on the brush border of the ileal enterocytes, which receptor would be involved in the adhesion of the AIEC LF82 strain.

D. Analysis of the Presence of Free Mannose Residues on the Brush Border of the Enterocytes Adhesin FimH, located on the type 1 pili, acts as a lectin and recognizes the mannosyl unit of the glycolipids or the glycoproteins expressed at the surface of the host cells. On this basis, concanavalin A (ConA) which binds specifically to the mannose residues was used to search for the presence of free mannose residues on the brush border of the enterocytes of the CD patients and the controls. The isolated enterocytes were incubated for 1 hour in PBS containing 50 μg/ml of ConA-FITC (ConA labeled with FITC, Sigma). After 4 washes, the enterocytes were observed under a fluorescence microscope at magnification×400.

The observation showed that the lectin binds to the brush border of the enterocytes of the CD patients. On the other hand, no binding of the lectin to the control enterocytes was observed, which demonstrates the expression of a highly mannosylated molecule on the brush border of the enterocytes of CD patients, which is not observed in the controls.

E. Expression of CD66c in Ileal Samples Obtained by Surgical Resection

Samples of inflammatory mucosa and of healthy mucosa were obtained by surgical resection on 20 CD patients and on 20 controls, respectively. Using fragments fixed with AFA (alcohol-formalin-acetic acid) and then embedded in paraffin and a preparation of 4 μm thin sections, immunolabelings were performed with the aid of an automated apparatus for immunolabeling with anti-CD66c antibodies (Ventana Medical System), using the method based on the avidin-biotin peroxidase complex. The sections were subjected to a 3 minute heat treatment under pressure in a pressure cooker in order to expose the epitopes.

The anti-CD66c monoclonal antibody clone 9A6 (Genovac, Switzerland) was used as antibody at the 1:50 dilution.

The sections were stained with Mayer's hematoxylin.

Figure 1:
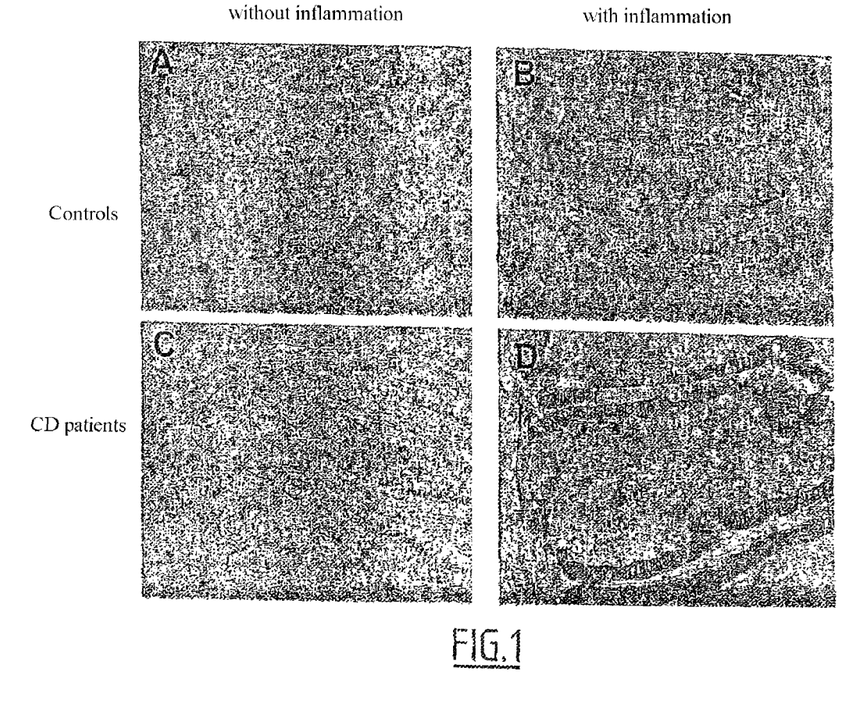
FIG. 1 represents ileal mucosa sections in subjects not suffering from an inflammatory bowel disease of the Crohn's disease or hemorrhagic rectocolitis type (1A and 1B) and in subjects suffering from Crohn's disease (1C and 1D).
Figure 2:
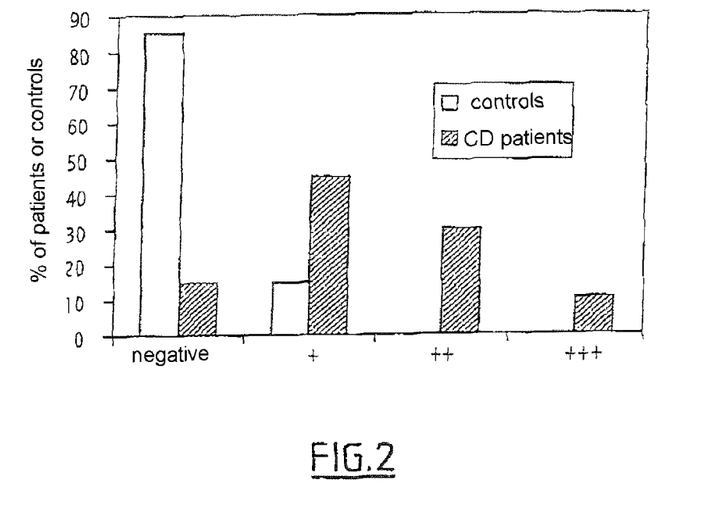
FIG. 2 is a graph representing the percentage of patients or control subjects showing labeling with anti-CD66c antibodies (according to the protocol of FIG. 1). The labeling is scored from − to +++ according to the intensity. It appears that 85% of the patients suffering from Crohn's disease abnormally express the CD66c receptor at the level of the ileum against only 15% of the healthy subjects.

The results are presented in FIGS. 1 and 2. 85% of the healthy subjects have no labeling with this CD66c antigen. On the other hand, the patients suffering from Crohn's disease show an overexpression of the CD66c receptors at the level of the brush border of the epithelial cells. This expression is very high in the case of mucosa exhibiting a high inflammation and ulcerations.

Example 2

Tests of Inhibition of the Adhesion of Bacteria

A. Assay of Inhibition by D-Mannose

The inhibitory power of D-mannose on the adhesion of the E. coli LF82 strain to the brush border of the enterocytes via the type 1 pili was tested. Adhesion trials were performed in the presence of 2% (w/v) D-mannose (Sigma) in MEM containing 10% FCS, the procedure being carried out as described above on enterocytes obtained from 3 CD patients (A, B and C) The results are presented in Table 3.

TABLE 3

| CD patients | Adhesion index without D-mannose | Adhesion index (% relative)[a] with 2% D-mannose |
|---|---|---|
| Patient A | 1.010 | 0.028 (2.7%) |
| Patient B | 1.511 | 0.032 (2.1%) |
| Patient C | 1.800 | 0.025 (1.4%) |

[a]percentage of the adhesion power of the wild-type LF82 strain in the presence of 2% D-mannose, compared with that in the absence of D-mannose, defined as representing 100%.

The addition of D-mannose causes a significant reduction in the index of adhesion of the LF82 strain to the brush border of the enterocytes of patients suffering from Crohn's disease.

Mutants of the LF82 strain, namely the mutant 52D11 not expressing type 1 pili and the ZG2 mutant not expressing the adhesin FimH, were also tested. These mutants have lost their capacity for adhesion to the brush border, as the results presented in Table 4 testify.

TABLE 4

| Bacterial strains | Inactivated gene | Adhesion index[a] (% relative)[b] on enterocytes of patient D | Adhesion index[a] (% relative)[b] on enterocytes of patient E |
|---|---|---|---|
| Mutant 52D11 | fimA | 0.100 (7.0) | 0.150 (10.6) |
| Mutant ZG2 | fimH | 0.095 (6.7) | 0.050 (3.6) |
| Wild-type LF82 strain | | 1.426 (100) | 1.404 (100) |

[a]mean number of bacteria adhering to the brush border of an enterocyte.
[b]percentage of adhesion power of the mutant compared with that of the wild-type LF82 strain, defined as representing 100%.

These results confirm that the type 1 pili, and more particularly the adhesin FimH of the LF82 strain are involved in adhesion to the brush border of the ileal enterocytes of patients suffering from Crohn's disease.

B. Trial of Inhibition by Antibodies

Monoclonal antibodies tested: anti-CD66c monoclonal (InnoGenex, Menarini Diagnostics, Anthony, France) and anti-CD48 monoclonal (PeliCluster, Tebu, Le Perray en Yvelines, France). These antibodies are used at the dilution 1/100 in MEM containing 10% FCS.

The enterocytes are pretreated for 30 min at 37° C. with the antibodies. The LF82 bacteria are then added and the adhesion trials performed as described above.

The results are presented in Table 5:

TABLE 5

| CD patients | Adhesion to the enterocytes in the presence of (% relative[a]) | | |
|---|---|---|---|
| | no antibody | anti-CD48 | anti-CD66c |
| Patient F | 1.450 ± 0.212 | 1.378 ± 0.174 (95.0) | 0.200 ± 0.067 (13.8) |
| Patient G | 1.145 ± 0.115 | 0.850 ± 0.050 (74.2) | 0.100 ± 0.033 (8.7) |
| Patient H | 1.016 ± 0.116 | 1.027 ± 0.027 (101.1) | 0.267 ± 0.067 (26.3) |
| Patient I | 1.283 ± 0.117 | 1.516 ± 0.051 (118.2) | 0.283 ± 0.050 (22.0) |

[a]percentage adhesion of the LF82 strain to the brush borders of enterocytes after preincubation with the various antibodies, compared with that obtained with enterocytes in the absence of antibody, defined as representing 100%.

The pretreatment with the anti-CD66c antibody causes the adhesion of the LF82 strain to decrease drastically. On the other hand, the anti-CD48 antibody does not affect the adhesion, indicating a specificity of the inhibition observed with the CD66c antibody. These results confirm that the adhesion of the LF82 strain to the ileal mucosa of CD patients involves a binding of the type 1 pili to the CD66c receptors overexpressed at the level of the brush border of the intestinal epithelial cells.

BIBLIOGRAPHIC REFERENCES

Audette, M., F. Buchegger, M. Schreyer, and J. P. Mach 1987. Monoclonal antibody against carcinoembryonic antigen (CEA) identifies two new forms of crossreacting antigens of molecular weight 90,000 and 160,000 in normal granulocytes Mol. Immunol. 24:1177-86.

Baert, F., Noman, M., Vermeire, S., Van Assche, G., G, D. H., Carbonez, A. and Rutgeerts, P. (2003) Influence of immunogenicity on the long-term efficacy of infliximab in Crohn's disease. N Engl J Med. 348: 601-608.

Beachey, E. H. (1981) Bacterial adherence: adhesin-receptor interactions mediating the attachment of bacteria to mucosal surface. J Infect Dis. 143: 325-345.

Bennett, R. A., Rubin, P. H. and Present, D. H. (1991) Frequency of inflammatory bowel disease in offspring of couples both presenting with inflammatory bowel disease. *Gastroenterology*. 100: 1638-1643.

Boudeau, J., A. L. Glasser, E. Masseret, B. Joly, and A. Darfeuille-Michaud 1999. Invasive ability of an *Escherichia coli* strain isolated from the ileal mucosa of a patient with Crohn's disease Infect Immun. 67:4499-509.

Boudeau, J., N. Barnich, and A. Darfeuille-Michaud 2001. Type 1 pili-mediated adherence of *Escherichia Coli* strain LF82 isolated from Crohn's disease is involved in bacterial invasion of intestinal epithelial cells Mol. Microbiol. 39:1272-84.

Colombel, J. F. and Mesnard, B. (1993) Maladie de Crohn. In: Editions Techniques, Encycl. Med. Chir. (Paris, France). *Gastroentérologie*. 9-057-G10: 1-15.

Darfeuille-Michaud, A., D. Aubel, G. Chauviere, C. Rich, M. Bourges, A. Servin, and B. Joly 1990. Adhesion of enterotoxigenic *Escherichia Coli* to the human colon carcinoma cell line Caco-2 in culture Infect Immun. 58:893-902.

Darfeuille-Michaud A. Adherent-invasive *Escherichia Coli*: a putative new *E. coli* pathotype associated with Crohn's disease. Int J Med Microbiol 2002; 292:185 93.

Darfeuille-Michaud, A., Neut, C., Barnich, N., Lederman, E., Di Martino, P., Desreumaux, P., et al (1998) Presence of adherent *Escherichia Coli* strains in ileal mucosa of patients with Crohn's disease. *Gastroenterology*. 115: 1405-1413.

Darfeuille-Michaud, A., Boudeau, J., Bulois, P., Neut, C., Glasser, A L., Barnich, N., Bringer, M A., Swidsinski, A., Beaugerie, L., Colombel, J F. High prevalence of adherent-invasive *Escherichia Coli* associated with ileal mucosa in Crohn's disease. Gastroenterology 2004, 127, 412-421.

Desreumaux, P., Brandt, E., Gambiez, L., Emilie, D., Geboes, K., Klein, O., et al (1997) Distinct cytokine patterns in early and chronic ileal lesions of Crohn's disease. *Gastroenterology*. 113: 118-126.

Glasser, A. L., J. Boudeau, N. Barnich, M. H. Perruchot, J. F. Colombel, and A. Darfeuille-Michaud 2001. Adherent Invasive *Escherichia Coli* Strains from Patients with Crohn's Disease Survive and Replicate within Macrophages without Inducing. Host Cell Death Infect Immun. 69:5529-37.

Grunert, F., S. Daniel, G. Nagel, S. von Kleist, and P. Jantscheff 1995. CD66b, CD66c and carcinoembryonic antigen (CEA) are independently regulated markers in sera of tumor patients. Int J Cancer. 63:349-55.

Guignot, J., I. Peiffer, M. F. Bernet-Camard, D. M. Lublin, C. Carnoy, S. L. Moseley, and A. L. Servin 2000. Recruitment of CD55 and CD66e brush border-associated glycosylphosphatidylinositol-anchored proteins by members of the Afa/Dr diffusely adhering family of *Escherichia Coli* that infect the human polarized intestinal Caco-2/TC7 cells Infect Immun. 68:3554-63.

Hammarstom, S., and V. Baranov. 2001. Is there a role for CEA in innate immunity in the colon? Trends in Microbiol. 9, 119-125.

Jantscheff P, Terracciano L, Lowy A, Glatz-Krieger K, Grunert F, Micheel B, Brummer J, Laffer U, Metzger U, Herrmann R, Rochlitz C. 2003. Expression of CEACAM6 in resectable colorectal cancer: a factor of independent prognostic significance. J Clin Oncol. 21:3638-46.

Köhler et Milstein, (1975), Nature (London), 256: 495-497

Kolbinger, F., K. Schwarz, F. Brombacher, S. von Kleist, and F. Grunert 1989. Expression of an NCA cDNA in NIH/3T3 cells yields a 110K glycoprotein, which is anchored into the membrane via glycosylphosphatidylinositol Biochem Biophys Res Commun. 161:1126-34.

Knutton, S., D. R. Lloyd, D. C. Candy, and A. S. McNeish 1985. Adhesion of enterotoxigenic *Escherichia Coli* to human small intestinal enterocytes Infect Immun. 48:824-31.

Lafeuille, B., A. Darfeuille, S. Petit, B. Joly, and R. Cluzel 1981. ["In vitro" study of attachment to human enterocytes in "*Escherichia coli*" strains isolated from infants with diarrheal disease (author's transl)] Ann Microbiol (Paris). 132B:57-6

Leusch, H. G., S. A. Hefta, Z. Drzeniek, K. Hummel, Z. Markos-Pusztai, and C. Wagener 1990. *Escherichia Coli* of human origin binds to carcinoembryonic antigen (CEA) and non-specific crossreacting antigen (NCA) FEBS Lett. 261:405-9.

Malaviya, R., Z. Gao, K. Thankavel, P. A. van der Merwe, and S, N. Abraham 1999. The mast cell tumor necrosis factor alpha response to FimH-expressing *Escherichia coli* is mediated by the glycosylphosphatidylinositol-anchored molecule CD48 Proc Natl Acad Sci USA. 96:8110-5.

Marks J D, Hoogenboom H R, Bonnert T P, McCafferty J, Griffiths A D, Winter G. 1991. By-passing immunization. Human antibodies from V-gene libraries displayed on phage. J. Mol. Biol. 222, 581-597.

Masseret, E., Boudeau, J., Colombel, J. F., Neut, C., Desreumaux, P., Joly, B., et al (2001) Genetically related *Escherichia Coli* strains associated with Crohn's disease. *Gut*. 48: 320-325.

Nakamura R M., Matsutani M., Barry M 2003. Advances in clinical laboratory tests for inflammatory bowel disease. Clinic Chimica Acta 335:9-20.

Nowicki, B., Hart, A., Coyne, K. E., Lublin, D. M. and Nowicki, S., Short consensus repeat-3 domain of recombinant decay-accelerating factor is recognized by *Escherichia coli* recombinant Dr adhesin in a model of a cell-cell interaction. *J Exp Med*, 178, 2115-21. (1993).

Podolsky D K. Inflammatory bowel disease. N Engl J Med 2002; 347:417-29.

Present, D. H., Rutgeerts, P., Targan, S., Hanauer, S. B., Mayer, L., van Hogezand, R. A., et al (1999) Infliximab for the treatment of fistulas in patients with Crohn's disease. *N Engl J Med*. 340: 1398-1405.

Rutgeerts, P., D'Haens, G., Targan, S., Vasiliauskas, E., Hanauer, S. B., Present, D. H., et al (1999) Efficacy and safety of retreatment with anti-tumor necrosis factor antibody (infliximab) to maintain remission in Crohn's disease. *Gastroenterology*. 117: 761-769.

Ryan P., Kelly R G., Lee G., Collins J K, O'Sullivan G C., O'Connell J O., Shanahan F. 2004. Bacterial DNA within granulomas of patients with Crohn's disease-Detection by laser capture microdissection. Am J Gastroenterology, 99: 1539-43.

Sartor R B, H. C. Rath, R. K. Sellon. Microbial factors in chronic intestinal inflammation. Current opinion in gastroenterology 1996; 12:327-333.

Sauter, S. L., S. M. Rutherfurd, C. Wagener, J. E. Shively, and S. A. Hefta 1991. Binding of nonspecific cross-reacting antigen, a granulocyte membrane glycoprotein, to *Escherichia Coli* expressing type 1 fimbriae Infect Immun. 59:2485-93.

Sauter, S. L., S. M. Rutherfurd, C. Wagener, J. E. Shively, and S. A. Hefta *Identification of the specific oligosaccharide sites recognized by type* 1 *fimbriae from E. coli on non-specific cross-reacting antigen, a CD66 cluster granulocyte glycoprotein. J Biol Chem*. 268(21):15510-6

Scott, J. K. and Smith, G. P., 1990, Searching for Peptide Ligands with an Epitope Library. Science, 249:386-390

Shanahan F. Crohn's disease. Lancet 2002; 359:62-9.

Shin, J. S, and S. N. Abraham 1999, *Bacteria-host cell interaction mediated by cellular cholesterol/glycolipid-enriched microdomains. Biosci Rep.* 19(5):421-32

Shin, J. S., Z. Gao, and S, N. Abraham 2000. Involvement of cellular caveolae in bacterial entry into mast cells Science. 289:785-8.

von Kleist, S., G. Chavanel, and P. Burtin 1972. Identification of an antigen from normal human tissue that crossreacts with the carcinoembryonic antigen. Proc Natl Acad Sci USA. 69:2492-4.

Wallis R S., Broder M S., Wong J Y., Hanson M E, Beenhouver D O 2004. Granulomatis infectious diseases associated with tumor necrosis factor antagonists. Clin Infect Dis. 38:1261-5.

The invention claimed is:

1. A method for treating Crohn's disease in a patient suffering from Crohn's disease and having an abnormal overexpression of the CD66c receptor at the ileal level comprising administering to said patient an effective amount of particles carrying one or more mannose units, wherein the particles carrying one or more mannose units inhibit the interaction between an adherent-invasive *E. coli* (AIEC) and the CD66c receptor expressed at the surface of the enterocytes of said patient, and wherein the particles are living cells, dead cells or inert beads.

2. The method of claim 1, wherein the particles are living cells.

3. The method of claim 1, wherein the particles are dead cells.

4. The method of claim 1, wherein the particles are inert beads.

5. The method of claim 1, comprising oral administration of the particles.

6. The method of claim 1, wherein the particles are included in tablets, capsules or granules, for immediate or controlled release.

7. The method of claim 1, wherein the particles carrying one or more mannose units inhibit the interaction between the type 1 pili of an AIEC *E. coli* and the CD66c receptor expressed at the surface of the enterocytes of a patient suffering from Crohn's disease.

8. The method of claim 1, wherein the particles carrying one or more mannose units inhibit the interaction between the FimH of an AIEC *E. coli* and the CD66c receptor expressed at the surface of the enterocytes of a patient suffering from Crohn's disease.

9. A method for inhibiting the interaction between an adherent-invasive *E. coli* (AIEC) and the CD66c receptor expressed at the surface of the enterocytes of a patient suffering from Crohn's disease and having an overexpression of the CD66c receptor at the ileal level, comprising administering to said patient an effective amount of particles carrying one or more mannose units, and wherein the particles are living cells, dead cells or inert beads.

10. The method of claim 1, wherein said patient has AIEC bacteria.

11. The method of claim 9, wherein said patient has AIEC bacteria.

* * * * *